United States Patent [19]

Harada et al.

[11] 4,447,543

[45] May 8, 1984

[54] METHOD FOR MEASURING VOLATILE HYDRIDES

[75] Inventors: Hikaru Harada, Kamakura; Teruo Akiyama; Tuneo Hiyama, both of Tokyo, all of Japan

[73] Assignee: Nippon Sanso K.K., Tokyo, Japan

[21] Appl. No.: 207,945

[22] Filed: Nov. 18, 1981

Related U.S. Application Data

[62] Division of Ser. No. 109,329, Jan. 4, 1980, Pat. No. 4,309,385.

[30] Foreign Application Priority Data

Jan. 26, 1979 [JP] Japan .................. 54-8027
Jan. 26, 1979 [JP] Japan .................. 54-8262[U]

[51] Int. Cl.$^3$ ............................ G01N 21/00
[52] U.S. Cl. ........................ 436/72; 422/91; 436/103; 436/164; 436/182
[58] Field of Search ............. 436/103, 114, 72, 182; 23/230 PC, 232 R, 232 E; 422/86, 91

[56] References Cited

U.S. PATENT DOCUMENTS

| | | | |
|---|---|---|---|
| 2,648,598 | 8/1953 | Stitt et al. .................. | 23/232 R |
| 3,844,719 | 10/1974 | Hammitt ..................... | 422/78 |
| 4,181,699 | 1/1980 | Kitzinger .................... | 422/91 |
| 4,271,125 | 6/1981 | Leichnitz .................... | 422/86 |

OTHER PUBLICATIONS

Anderson, Reactions of Triethyltin Hydride with Inorganic Halides and Oxides; J.A.C.S. 9-20-57; pp. 4913-4915, vol. 79.
Det. Tube Handbook 4th Ed., 1979, Leichnitz.

*Primary Examiner*—Michael S. Marcus
*Attorney, Agent, or Firm*—Darby & Darby

[57] ABSTRACT

According to the present invention volatile hydrides such as diborane, arsine, phosphine and the like are made to react with mercuric oxide at room temperature to produced mercury atom, the concentration of which is thereafter measured and the concentration of volatile hydrides is determined in accordance with the corresponding measured mercury atom concentration. As the measuring apparatus according to the present invention is made to measure mercury atom, it can easily detect even extremely small quantity of substances such as volatile hydrides and respond quickly, thus enabling the apparatus to be suitably used as a monitor in semiconductor industry.

2 Claims, 2 Drawing Figures

METHOD FOR MEASURING VOLATILE HYDRIDES

This is a division of application Ser. No. 109,329, filed Jan. 4, 1980, now U.S. Pat. No. 4,309,385.

BACKGROUND OF THE INVENTION

The present invention relates to a method for measuring such volatile hydrides as diborane ($B_2H_6$), arsine ($AsH_3$), phosphine ($PH_3$), stibine ($SbH_3$), hydrogen selenide ($SeH_2$), monosilane ($SiH_4$) and the like which are broadly used as doping material or epitaxializer in the field of semiconductor industry.

Hitherto, the following methods for measuring volatile hydride concentration have been known (1) colorimetric methods (methods of chemical analysis) based primarily upon their reaction with reagents, (2) infrared methods utilizing the property of the gas molecule to be examined to absorb the infrared rays, (3) ultraviolet methods utilizing the property of the gas molecule to be examined to absorb ultraviolet rays, and (4) the atomic absorption method based on measuring the light absorption of an atomic molecule caused by thermal decomposition of the gas to be examined. However, colorimetric methods have weak points such as complicated and time consuming measuring operations. Both the infrared and the ultraviolet method both of them proved to have poor measurement sensitivity in that amounts as high as several ppm could only be measured with difficulty by these methods. The atomic absorption method was inconvenient in various ways for example, high temperature on the frame was unavoidable, apparatus was expensive and the like. As mentioned above, none of the hitherto known methods for measuring volatile hydrides could bring about a satisfactory result. Further, measurement of extremely small quantities of hydrides was considered extremely difficult or almost impossible. These compounds are strongly toxic, the tolerance limit or allowable concentration is generally considered to be ranging between about 0.1 ppm. For example, the limit 0.05-0.3 ppm (50-300 ppb), for arsine is 0.05 ppm; and for phosphine it is 0.3 ppm for stibine it is 0.1 ppm for hydrogen selenide it is 0.05 ppm; and for diboran 0.1. Detection and accurate measurement of these compounds were difficult. Especially diborane had been considered to be almost impossible to measure. In view of the fact that volatile hydrides are broadly used these days, the above situation was not desirable for health maintenance reasons.

SUMMARY OF THE INVENTION

It is an object of the present invention to provide a method for measuring volatile hydrided said method being capable of measuring easily and accurately even extremely small quantities of hydrides which had hitherto been difficult or almost impossible to measure. Another object of the invention is to provide to measure for carrying out said method of measurement which can be followed in a simple manner and which can effect such measurements in a short period of time inexpensively without necessitating use of high temperature heating. The first characteristic of the present invention is that volatile hydrides are made to react with mercuric oxide to produce atomic mercury, the concentration of mercury atoms is thereafter measured and the concentration of volatile hydrides is determined according to the corresponding concentration of mercury atoms. The measurement method of the present invention is hence suitable for industrial use. The present invention is characterized next by a measuring method comprising a reaction step in which volatile hydrides are made to react with mercuric oxide, and the mercuric oxide is thereby converted to atomic mercury, and a detection step in which the concentration of the mercury atoms produced by this reaction is measured by ultraviolet spectroscopic analysis.

DETAILED DESCRIPTION OF THE INVENTION

Figure 1:
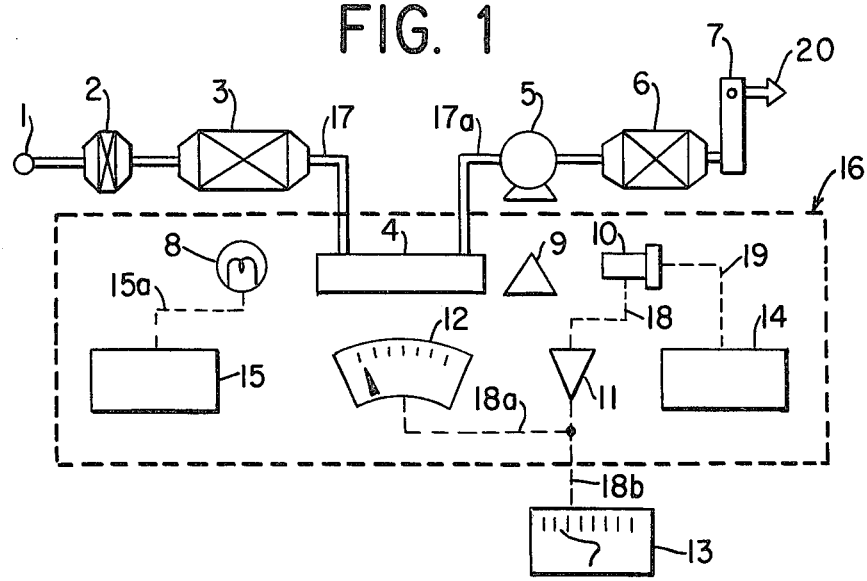

To begin with, volatile hydrides such as diborane, arsine, phosphine, hydrogen selenide and monosilane contained in an inert gas like nitrogen or in air are made to react with a stoichiometric excess of mercuric oxide at an ordinary temperature, the mercuric oxide being thereby converted to atomic mercury. The reactions between volatile hydrides above mentioned are considered to proceed in accordance with the following scheme:

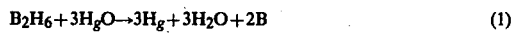
$$B_2H_6 + 3H_gO \rightarrow 3H_g + 3H_2O + 2B \tag{1}$$

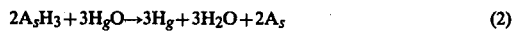
$$2A_sH_3 + 3H_gO \rightarrow 3H_g + 3H_2O + 2A_s \tag{2}$$

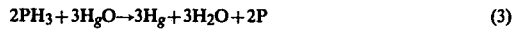
$$2PH_3 + 3H_gO \rightarrow 3H_g + 3H_2O + 2P \tag{3}$$

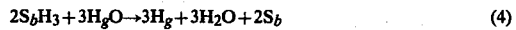
$$2S_bH_3 + 3H_gO \rightarrow 3H_g + 3H_2O + 2S_b \tag{4}$$

$$S_eH_2 + H_gO \rightarrow H_g + H_2O + S_e \tag{5}$$

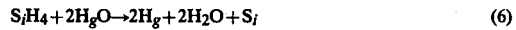
$$S_iH_4 + 2H_gO \rightarrow 2H_g + 2H_2O + S_i \tag{6}$$

The concentration of the mercury atoms generated through these reactions is proportional to the concentration of volatile hydrides and can be meansured by means of ultraviolet spectroscopic analysis. The concentration of volatile metallic hydrides is thereby determined by comparison with the corresponding concentration of measured mercury. As mercury atoms are easily detected even in a extremely samll quantities, detection of volatile hydrides can be easily performed. Further, as shown in the above formulas (1)-(6), although 1 mol of hydrogen selenide, thereof produces only 1 mol of mercury 1 mol of diborane produces 3 mols of mercury, 1 mol of monosilane produces 2 mols of mercury and further in case of arsine, phosphine and stibine each mol thereof produces 1.5 mols of mercury. In case of gases other than those including hydrogen selenide, the mercury atoms generated per mol of volatile hydrides amounts to 1.5-3 mols, thus making it possible for these hydrides to be detected and determined with high sensitivity. By recording and indicating the data obtained through the above-described detection method, the concentration of volatile hydrides is determined easily and accurately.

Figure 2:
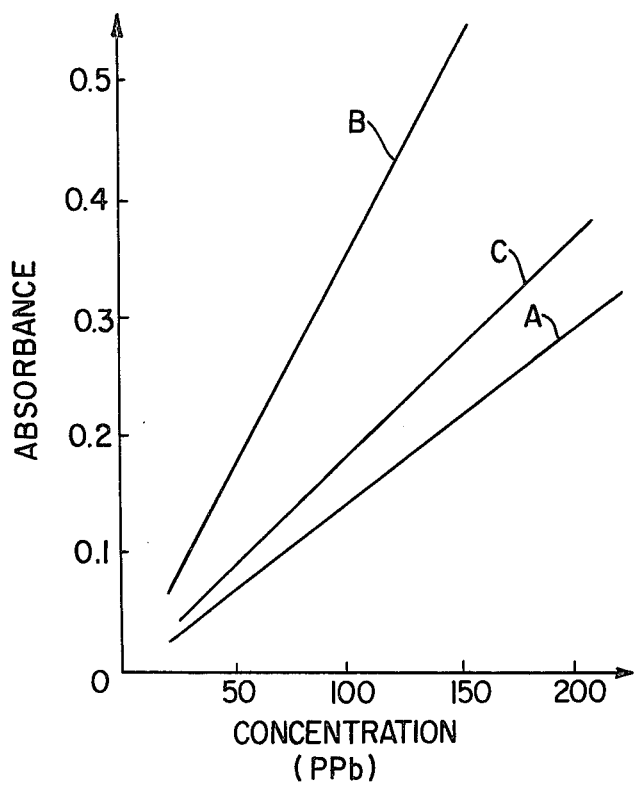

FIG. 2 is a diagram of the relation between the absorbance of mercury atoms and concentrations of mercury, diborane, arsine and phosphine found by experiment. First, several samples with known mercury concentrations were prepared and then absorbance of mercury was measured on each by means of the ultraviolet absorption method and the obtained results were plotted. Consequently, a calibration curve was obtained as illustrated by curve A.

On the other hand, several samples with known concentration were prepared beforehand for diborand, arsine and phosphine, respectively, and made to react with mercuric oxide. Absorbances of obtained mercury were measured and plotted respectively. Curve B was obtained for diborane and Curve C for arsine or phosphine. By comparison of Curves A, B and C illustrated in FIG. 2, it was found that 1 mol of diborane produced about 3 moles of mercury, while 1 mol of arsine or phosphine produced about 1.5 mols of mercury In this way, it was confirmed that reactions actually proceeded according to the above schemes (1)–(3).

Next, samples containing diborane, arsine and phosphine with unknown concentrations of a rank as low as ppb were each made to react with mercuric oxide and the absorbance of mercury produced thereby was measured by means of an ultraviolet absorption based on the obtained absorbance of mercury, concentrations of the hybride were found by use of Curve A. Subsequently, the concentration of diborane was calculated by multiplying the atomic mercury concentration by $\frac{1}{3}$, and those of arsine and phosphine by $\frac{2}{3}$. It was thus confirmed that even concentrations as low as ppb can be measured easily and accurately. In the above embodiment mercury atoms were measured by the ultraviolet absorption method. However, the above embodiment was merely an example and other measuring methods may also be employed.

An embodiment of the apparatus according to the present invention will be explained in detail below by reference to FIG. 1.

The measuring apparatus of the present invention comprises a sample-introducing part into which samples containing a volatile hydride (such as diborane, arsine, phosphine, stibine, hydrogen selenide or monosilane) in an inert gas like nitrogen and air, are introduced, a reaction part in which volatile hydrides are made to react with mercuric oxide thereby converting the mercuric oxide to atomic mercury, a detection part in which the mercury atom concentration generated in the reaction part is detected by the ultraviolet absorption method, an indicating and recording part in which the mercury atom concentration detected in the detection part is indicated and recorded and the concentrations of volatile hydrides are determined by reference to to the mercury atom concentration, and a discharge part in which the already detected gases inclusive of atomic mercury are discharged after removal of poison.

Said sample introducing part is composed of a gas entrance 1 and a dust eliminator 2 which is connected by way of duct 17 to the gas entrance 1. Said reaction part comprises of mercuric oxide reaction cell 3 which is connected to said dust eliminator 2 by way of gas duct 17 and is filled with pulverized mercuric oxide. Further, said detection part, being an apparatus known as an atomic absorption analyzer 16, comprises a light absorption cell (quartz window) 4 connected to said mercuric oxide reaction cell 3 by way of gas duct 17, an ultraviolet radiation source 8, such as a mercury low-voltage discharge lamp, or a mercury hollow cathode lamp, for the purpose of radiating ultraviolet rays into the light absorption cell 4; a power supply 15 connected to said ultraviolet radiation source 8 by way of a power supply circuit 15a, a wave length selector 9 such as a (diffraction grating) spectroscope or an interference filter, a light receiver bulb 10 such as an electron multiplier tube, a photoelectric tube and a photo-electric element and a high voltage power supply 14 connected to said light receiver bulb 10 by way of power supply circuit 19.

Further, the aforesaid indicating and recording part comprises a signal operation amplifier 11 connected to said light receiver bulb 10 by way of electric signal circuit 18, a concentration index gauge 12 connected to the signal operation amplifier 11 by way of electric signal circuit 18a and an indicating and recording gauge 13 connected to the same amplifier 11 by way of another electric signal circuit 18b which branches from said electric signal circuit 18a.

Further, the above mentioned discharge part comprises a gas-pump 5, a depoisoner 6, a flowmeter 7 and a gasexit 20, all being incorporated in a gas passage 17a that derives from light absorption cell 4.

The operation of the measuring apparatus according to the present invention will be described hereunder.

Initially, a gaseous sample containing volatile hydrides mixed with an inert gas like nitrogen or air, is introduced from gas entrance 1 and is led into the mercuric oxide reaction cell 3 after being freed of dust in the dust eliminator 2. Volatile hydrides in the sample gas thus introduced into the reaction cell 3 are made to react with the mercuric oxide filling the inner space of the cell 3 thereby converting the mercuric oxide to mercury atom. Next, the sample gas, which contains vaporous atomic mercury generated in cell 3, is transferred via gas duct 17 to light absorption cell (quartz window) 4. The ultraviolet radiation source 8 activated by the help of the power supply 15, causes ultraviolet rays to be radiated into light absorption cell 4. After having been received by wave length selector 9 the rays are received in light receiver bulb 10 operated by high voltage power supply 14. The signal coming through electric signal circuit 18 is amplified by signal operation amplifier 11 and the amplified signal is put into concentration index gauge 12 via the electric signal circuit 18(a) and also into indicating and recording gauge 13 by way of electric signal circuits 18a and 18b. In addition, the gas passed through said light absorption cell 4, is transferred from the gas passage 17a by actuating gas pump 5 to depoisoner 6 and after being depoisoned therein is discharged from gas exit 20.

The mercury concentration indicated in the concentration index gauge through the operation described above is multiplied by $\frac{1}{3}$, for example, in case of diborane and $\frac{2}{3}$ in case of arsine and phosphine in accordance with the reaction schemes or the diagram in FIG. 2, and each figure thus obtained represents the concentration of the volatile hydrides. When the measuring substances is specified, the scale of the concentration index gauge 12 and of indicating and recording gauge may be appropriately adjusted beforehand so that the concentration of volatile hydride can be read off the gauge immediately.

Further, although the above description has been based on the measurement of gaseous hydrides, the present invention is not limited thereto as powders and solutions of metals such as As and Pb which are convertible into volatile metallic hydride by means of a proper apparatus like a reductive vaporizer can likewise be detected and measured according to the present invention.

As explained hereinbefore volatile hydrides to react with mercuric oxide to produce atomic mercury, the concentration of volatile metallic hydride being determined by reference to the measured mercury atom concentration. Even very small quantities of atomic mercury can be easily detected. In addition for most of the volatile hydrides, 1 mole of hydride produces 1.5 to 3 moles of atomic mercury. Therefore, the measurement can be carried out with so high sensitivity that even extremely small quantities, such as the like the tolerance limit or allowable concentration for a hydride can be detected and determined easily and accurately. Hydride measurement according to the present invention has a further advantage in that it can be carried out at ordinary temperatures and by a simple operation and in a short time. Further, the apparatus according to the present invention is a gauge capable of being used in industry, because it is a monitor with high sensitivity good for the purpose of securing health of workers and maintaining safety of environment in the field of semiconductor industry or the like where volatile hydrides are handled. In addition, its price is moderate, especially with respect to diborane. Since no practical apparatus had been provided for measuring very small quantities of volatile hydrides, employment of the present invention will significantly affect the industries concerned. When the apparatus is used as a monitor, the aforementioned concentration index gauge 12 and indicating and recording gauge 13 are unnecessary and it may well be so constructed as to generate a signal when the concentration of hydrides is detected to exceed the threshold limit value and send the signal directly to an alarm circuit. Further, it is recommendable to use a mercury low-voltage discharge lamp as an ultraviolet radiation source, an interference filter as a wave length selector and a photo-electric tube or photo-electric element as a light receiver bulb for a low priced apparatus.

What is claimed is:

1. A method for measuring the concentration of hydrides selected from the group consisting of diborane, arsine, phosphine, stibine, hydrogen selenide and monosilane, comprising reacting said hydrides with an excess of mercuric oxide at an ambient temperature to form stoichiometric amounts of gaseous atomic mercury, water and the element consisting of the non-hydrogen constituent of said hydrides measuring the amount of said atomic mercury and determining the concentration of said hydrides by reference to the amount of said atomic mercury produced and the stoichiometric ratios for said reaction; wherein the lower limit of the quantity of said hydrides capable of measurement by said method is below the allowable concentration for said hydrides.

2. A method according to claim 1, wherein said atomic mercury concentration is measured by ultraviolet absorption.

* * * * *